United States Patent [19]

Deucher et al.

[11] Patent Number: 5,220,588
[45] Date of Patent: Jun. 15, 1993

[54] LOW INERTIA BRUSH BLOCK ASSEMBLY

[75] Inventors: Joseph S. Deucher, Lyndhurst; Leonard J. Visdos, Chagrin Falls; Anton Z. Zupancic, Kirtland, all of Ohio

[73] Assignee: Picker International, Inc., Highland Hts., Ohio

[21] Appl. No.: 710,831

[22] Filed: May 20, 1991

[51] Int. Cl.$^5$ .............................................. G03B 41/16
[52] U.S. Cl. ......................................... 378/15; 378/4; 378/194; 439/13; 439/28
[58] Field of Search ................... 378/4, 15, 20, 194; 439/13, 24, 21

[56] References Cited

U.S. PATENT DOCUMENTS

| | | | |
|---|---|---|---|
| 4,323,292 | 4/1982 | Lewis et al. | 439/28 |
| 4,352,530 | 10/1982 | Dinwiddie et al. | 378/15 |
| 4,544,215 | 10/1985 | Fritsch | 439/13 |
| 4,644,573 | 2/1987 | Palermo et al. | 378/15 |
| 4,779,469 | 10/1988 | Ashley | 439/13 |

OTHER PUBLICATIONS

Product Bulletin, The Polymer Corporation, Reading, Pa., BR 17-B, Nov. 1987.
Picker International Drawing Nos. D 97410; D 97634; D 171765; and D 171766 (Four Sheets).

Primary Examiner—David P. Porta
Assistant Examiner—Kim-Kwok Chu
Attorney, Agent, or Firm—Fay, Sharpe, Beall, Fagan, Minnich & McKee

[57] ABSTRACT

The power brush block assembly (26) and a communication signal brush block assembly (28) are mounted to a rotating gantry portion (20) of a CT scanner in sliding communication with a stationary slip ring (16). The power communication brush block includes a plurality of like mounting blocks which when interconnected together in alignment define a locator aperture (64') and a shaft aperture (26') in radial alignment. A brush (70) includes a tip (72) and a shaft (76) around which a coil spring (100) is slidably received. The brush and spring assemblies are slidably received through the locator aperture until the brush tip is in sliding communication therewith and the shaft is in sliding communication with the shaft aperture. A retainer (102) prevents the spring from propelling the brush completely through the locator aperture. An electrical lead (104, 104') has a friction connector (106) which is connected to one end (78) of the brush shaft and connected at its other end with an electrical contact (88, 88'). In the power brush block assembly, the locator and shaft apertures are defined by mounting together like mounting blocks (110). In the communication signal brush block assembly, the locator and shaft apertures are defined in circuit boards (60, 80) which are held in an arcuate figuration by identical spacer plates (44). Identical side plates (42) interconnect the slide plates and to provide a mounting arrangement for mounting the brush block to the rotating gantry portion.

19 Claims, 6 Drawing Sheets

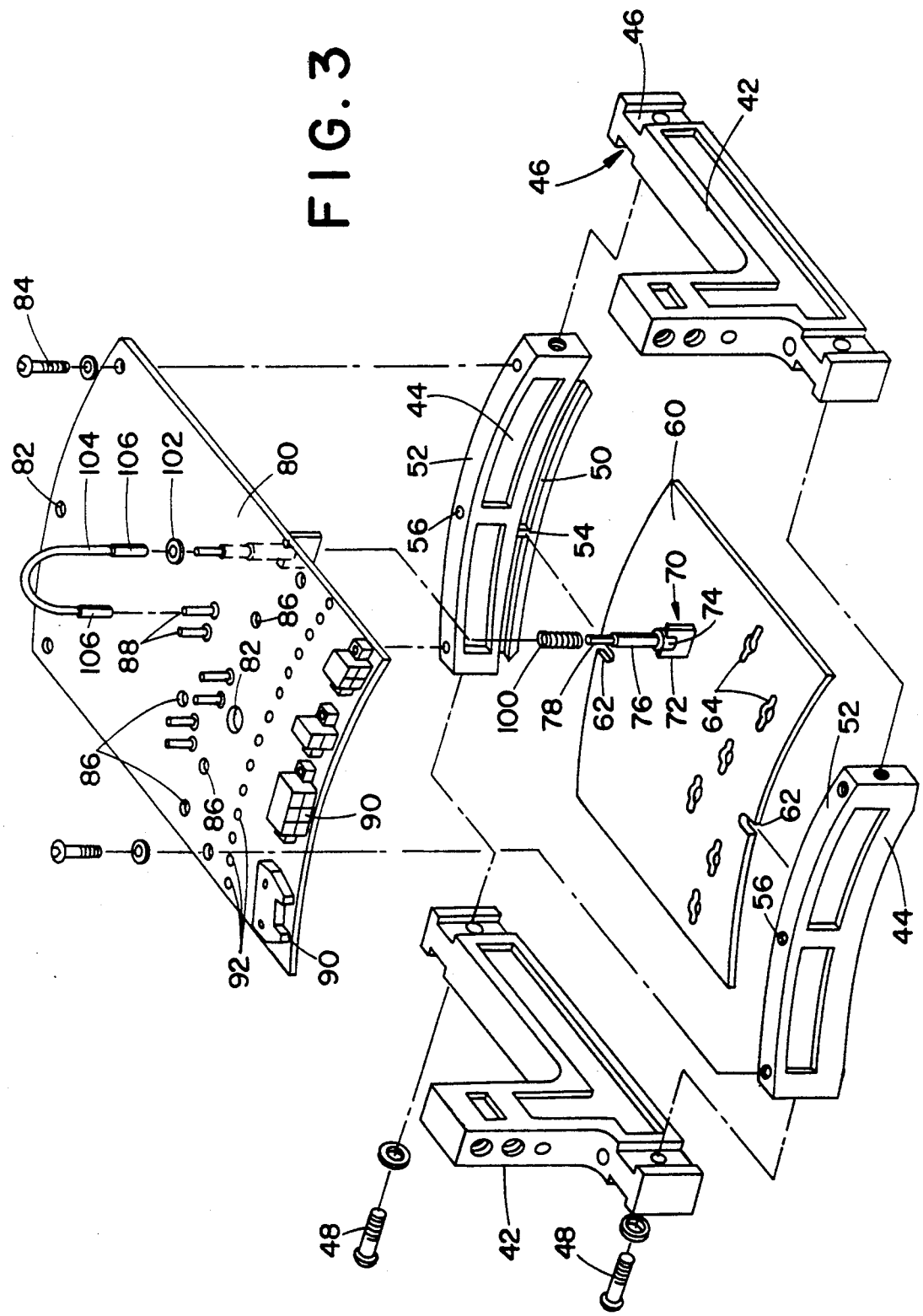

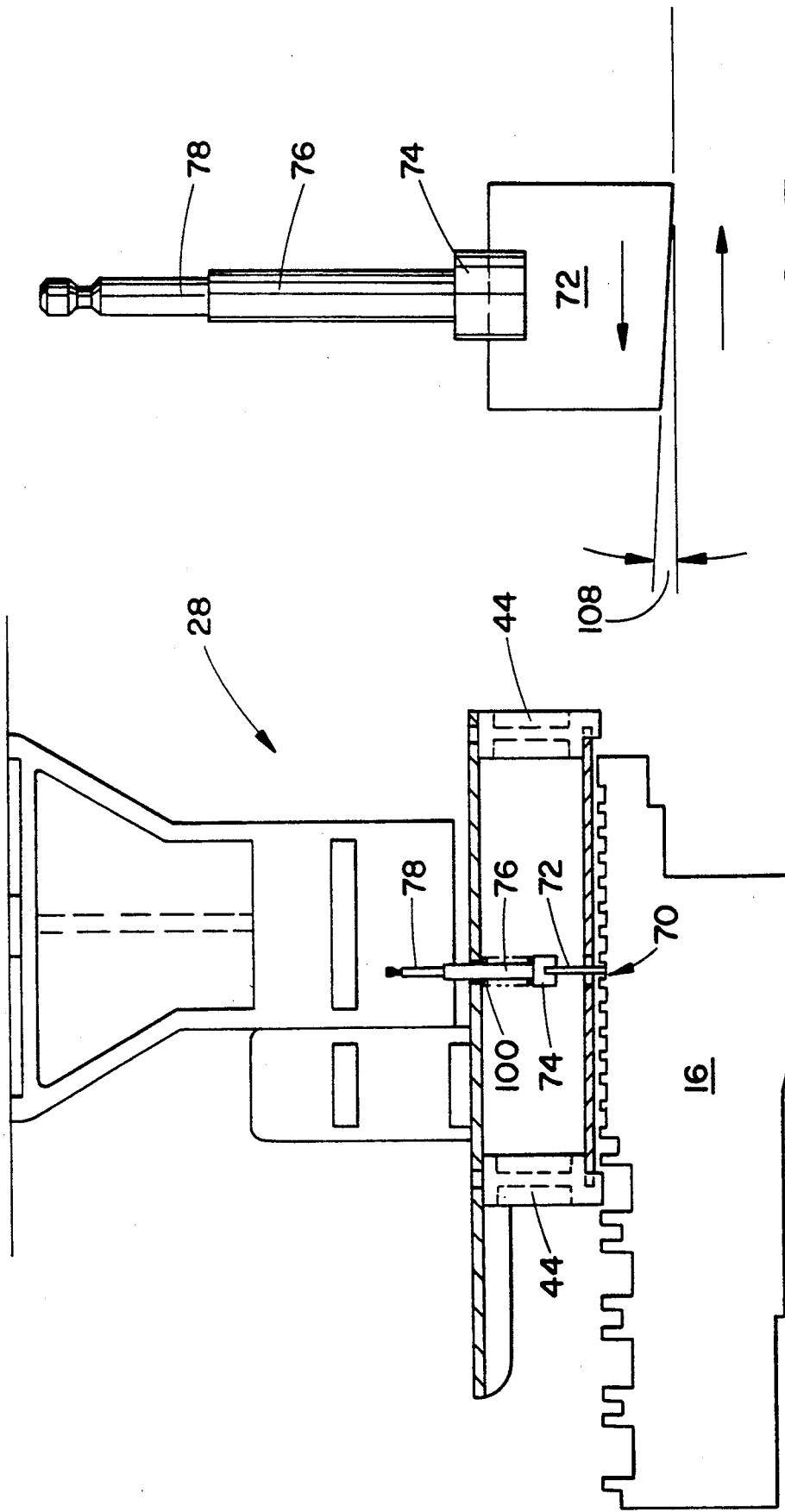

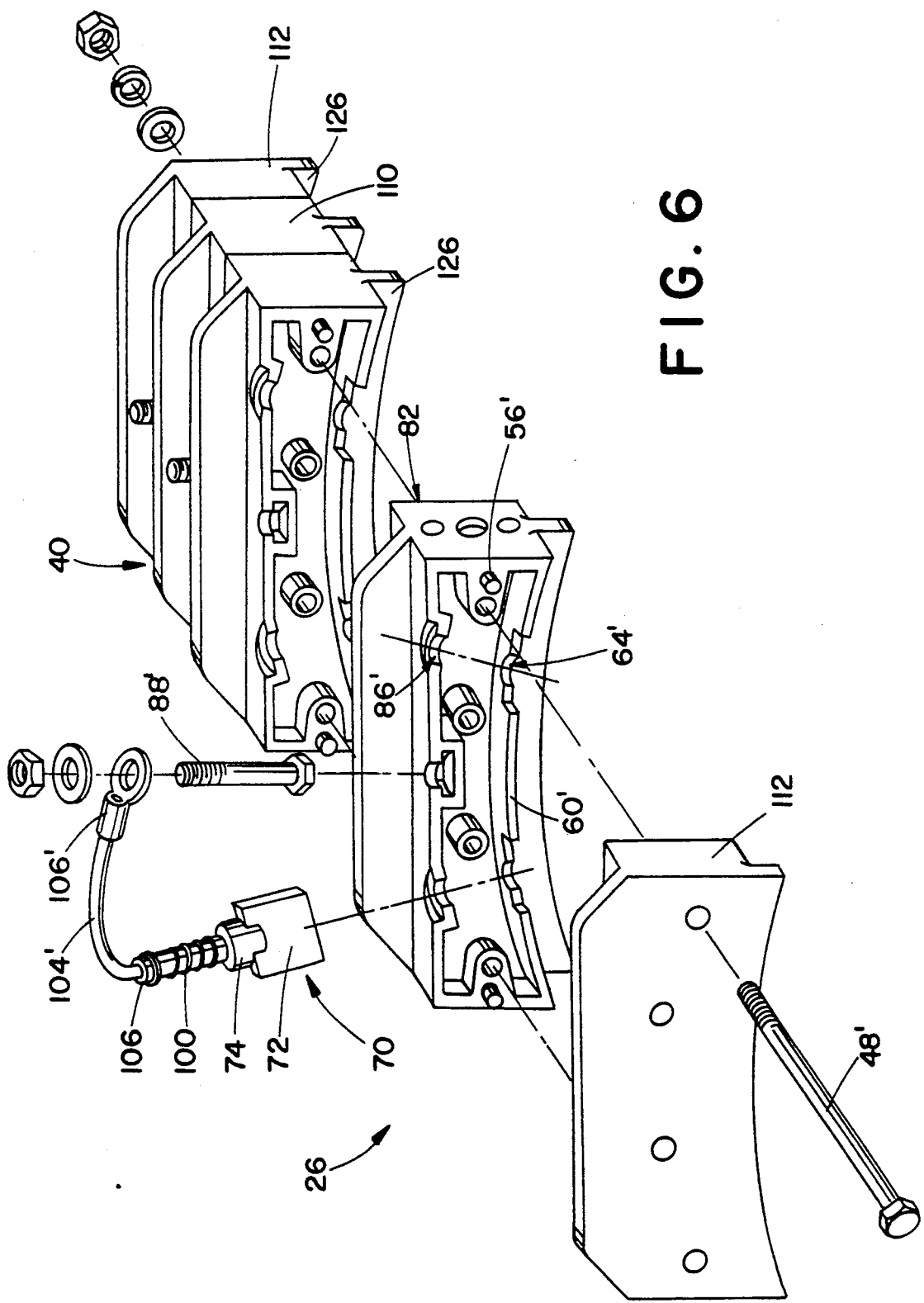

LOW INERTIA BRUSH BLOCK ASSEMBLY

BACKGROUND OF THE INVENTION

The present invention pertains to the art of power transfer, particularly the transfer of electrical power between structures which are moving relative to one another. The invention finds particular application in conjunction with brush block assemblies for transferring high voltage electrical power and lower voltage electrical communication signals between the stationary and rotating gantry portions of CT scanners and will be described with particular reference thereto. However, it is to be appreciated that the present invention will also find application in conjunction with brush block assemblies for transferring power or communication signals in other environments.

Typically, a CT scanner has a center bore of 65 centimeters around which large diameter slip rings on the order of 70-75 centimeters in diameter are stationarily mounted. The x-ray tube is mounted in a rotating gantry portion mounted on bearings for rotation around the central cylinder. Arrays of brush assemblies were mounted to the rotating gantry portion to make electrical contact with the stationary slip rings in order to transfer high voltage electric power for operating the x-ray tube and electrical communication signals between the stationary rotating gantry portions.

One type of prior art brush blocks uses wire brushes. A wire brush consists of one or more wires arranged such that they function as a cantilever beam with its free end positioned against the conductive ring. Commonly, two brushes were used per ring to increase the current carrying capacity.

Wire brush assemblies are very delicate and easily damaged both before and during installation. Individual brush assemblies are not replaceable. Rather, the entire, relatively expensive brush block must be replaced. Wire brush assemblies use different slip ring arrangements than other brushes. Specifically, the slip ring is commonly a u-shaped groove whose inner surface is designed to contain and guide the wires during rotation in the normal direction. When the brush assemblies are changed to a different type of brushes, new slip rings must also be installed. Under rotation opposite to the normal direction, the wire brushes may hang up, buckle, and experience sudden catastrophic failure. High current overloads can vaporize the wires.

Another type of prior art brush is the composite brush. Composite brushes are commonly sold as a cartridge, i.e. a housing within which a block of conductive silver-graphite alloy material is slidably received. A cantilever, compression, constant force, or other spring is mounted within the housing to urge the block to extend, i.e. into contact with the slip ring.

One problem with the composite brushes is that the cartridges are relatively bulky. In many applications, such as CT scanner, the use of redundant cartridges, i.e. two brushes per ring, requires unacceptably large physical dimensions. When using only one brush per ring, the brush is apt to skip causing signal loss on communications signals or arcing on high voltage signals. In an effort to reduce the signal loss and arcing, relatively high spring pressures are used in the cartridge to bias the brushes hard against the slip rings. The high spring pressures decrease brush life due to a high frictional wear between the brush and the slip ring. The high friction quickly grinds the brush into conformity with a circular arc of the slip ring and wears it down leaving brush debris in the slip ring channels. Another problem with the cartridges is that the brush tends to hang up or stick. The cartridges tend to be relatively shallow compared to the length of the brush. Even small amounts of canting or tipping force from interaction with the slip ring can cause the brush to hang up or stick.

The present invention contemplates a new and improved brush block assemblies which overcomes the above referenced problems and others.

SUMMARY OF THE INVENTION

In accordance with one aspect of the invention, a modular brush block frame assembly is provided. In one embodiment, identical molded plastic left and right side pieces are interconnected with identical forward and rearward molded plastic spacer pieces. Two sheets of printed circuit board material are laid flat, precision drilled, and arced into conformity with the slip ring diameter. The arced boards are mounted to upper and lower surfaces of the modular frame assembly. Brush assemblies are slidably received through aligned apertures in the upper and lower arced circuit board material.

In accordance with another aspect of the present invention, a plurality of like molded plastic blocks are aligned and connected together. Adjoining pairs of the molded block define upper and lower radially aligned apertures through which a brush assembly is slidably received.

In accordance with another aspect of the present invention, each brush assembly includes an enlarged tip of conductive material which is joined to an elongated post. The post and the tip are slidably received in the radially displaced upper and lower apertures or guides.

In accordance with a more limited aspect of the invention, the enlarged tip is constructed of a silver-/polymeric alloy which has good electric conductivity, low inertia, and is self-lubricating by the polymeric material.

In accordance with another aspect of the present invention, an end of the post opposite the tip receives a snap fit electrical connection on the end of an electrical shunt wire. The shunt wire is arced in a wide arc and connected to an electric connection post. The wide arc of the wire allows free movement of the brush while preventing fatiguing of the wire.

In accordance with another aspect of the invention, the brush tip has a low mass and is biased toward the slip ring with a low pressure. A slip ring contacting edge of the brush tip is cut on a bevel such that the brush contacts the slip ring behind its axis, i.e. the brush is trailing or dragging along the slip ring.

One advantage of the present invention is its long brush life.

Another advantage of the present invention is that the brush tips resist bouncing, eliminating audible noise and arcing.

Another advantage of the present invention is that it facilitates replacement of individual brushes in the field.

Another advantage of the present invention is that shunt wiring is simplified. The shunt wiring is of equal length, does not touch or cross other shunt wiring, and offers little resistance to brush movement.

Still further advantages of the present invention will be come apparent to those of ordinary skill in the art upon reading and understanding the following and detailed description of the preferred embodiments.

BRIEF DESCRIPTION OF THE DRAWINGS

The invention may take form in various parts and arrangements of parts and in various steps and arrangement of steps. The drawings are only for purposes of illustrating the preferred embodiment and are not to be construed as limiting the invention.

FIG. 3 is an exploded view of one embodiment of a brush block assembly with all but one brush eliminated for simplicity of illustration in accordance with the present invention that is particularly adapted for communication signals;

FIG. 4 is a sectional view through section 3—3 of FIG. 2 with only a single one of the 28 brushes illustrated for simplicity of illustration;

FIG. 5 is an elevational view of one of the brushes;

FIG. 6 is an exploded view of another embodiment of the present of a brush block assembly in accordance with the present invention particularly adapted for high voltage power signals;

DETAILED DESCRIPTION OF THE PREFERRED EMBODIMENTS

Figure 1:
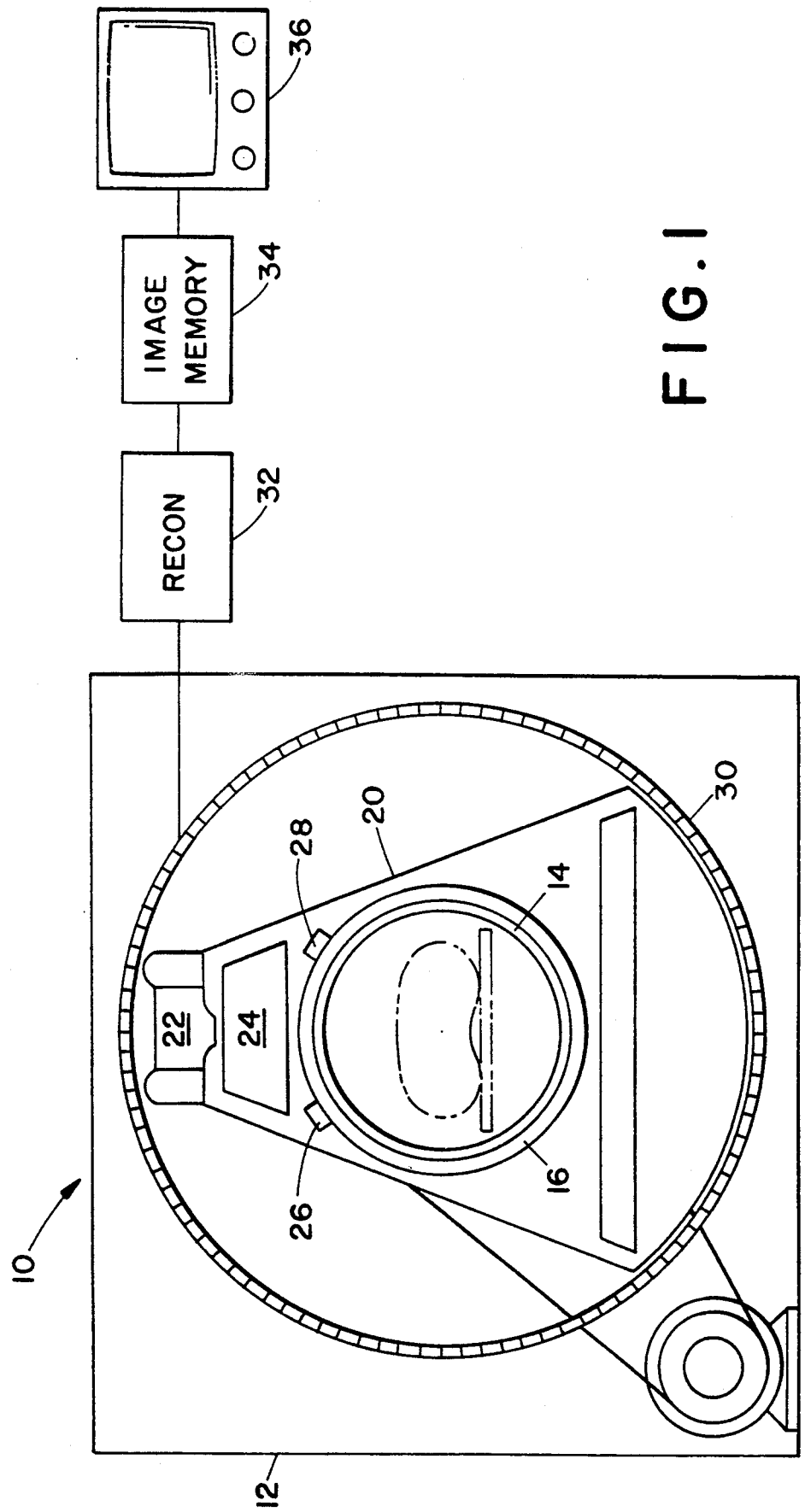
FIG. 1 is a diagramatic illustration of a CT scanner with brush blocks in accordance with the present invention.

With reference to FIG. 1 a CT scanner 10 includes a stationary frame portion 12 including a stationary, central patient receiving cylinder 14 that defines an examination region. A slip ring assembly 16 is disposed around the stationary cylinder.

A rotating gantry portion 20 is mounted on bearings (not shown) to the stationary cylinder. The rotating gantry portion includes an x-ray tube 22. A shutter and collimator 24 shapes the emitted radiation into a fan shaped sheet directed centrally through the cylinder and selectively gates the radiation through the examination region and blocks it. A power brush block assembly 26 carries high voltage power from a power source to the x-ray tubes. A communications brush block assembly 28 transfers communication signals between the rotating and stationary gantry portions. The communication signals may include control signals with a shutter and collimator unit for opening and closing a shutter portion thereof, output signals from x-ray tube operating parameter monitors for carrying signals descriptive of the operation of the x-ray tube, and the like.

Radiation which has traversed an examination region defined within the stationary cylinder impinges upon a ring of stationary detectors 30. Alternately, an arc of detectors may be mounted on the rotating gantry portion spanning the arc of the fan beam. Detectors mounted on the rotating gantry portion are connected with the signal brush block assembly 28. A multiplicity of signal brush block assemblies may be provided if necessary for the large number of signals in question. The output from the detectors is reconstructed by an imaging or reconstruction means 32 which applies a conventional reconstruction algorithm, such as a convulsion and back rejection algorithm. The image representation is stored in an image memory 34 for display on a video monitor 36.

Figure 2:
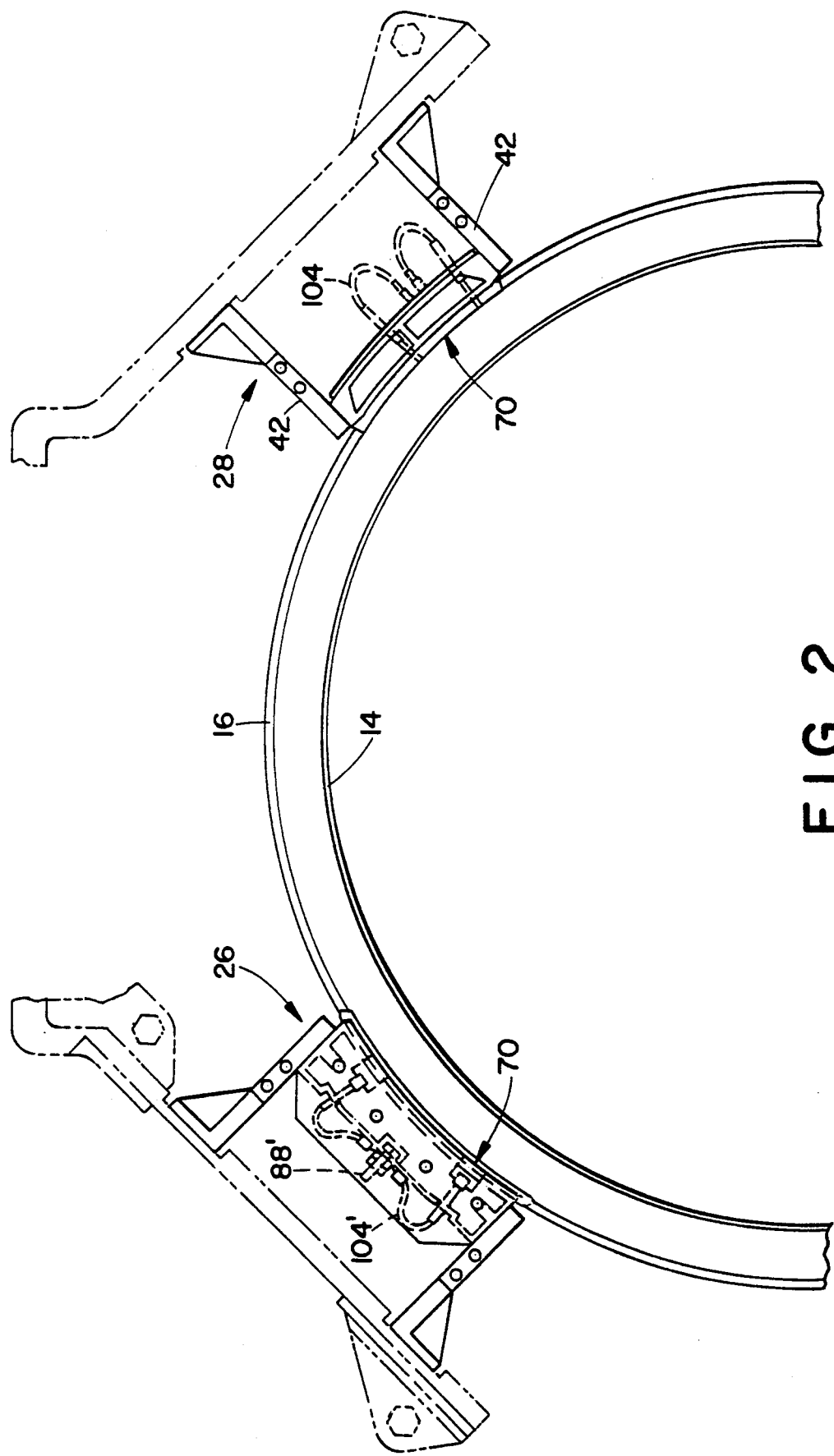
FIG. 2 is a side view of power and communications brush block assemblies of FIG. 1 in combination with a segment of a large diameter slip ring.

With particular reference to FIGS. 2, 3, and 4 the signal brush block assembly includes an outer frame portion 40 including a pair of like side plates 42 and a pair of like end spacer plates 44. The side plates 42 have the same molded configuration on both sides such that a single mold molds plastic plates which are suitable for use on either side. Note for example that the side plates have grooves 46 on both sides within which respective ends of the spacer plates are received and anchored by threaded fasteners 48.

The spacer plates 44 define an arcuate groove 50 which matches the arc of the slip ring and define a second arcuate surface 52 which is also an arc segment defined concentrically with the slip ring, i.e. concentric to arcuate groove 50. An alignment means such as a rib 54 and a pin or projection 56 define a center of the spacer members symmetrically. Note that the spacer members can be reversed or rotated 180° about their center to be used on either side of the frame.

A first or lower piece of printed circuit board 60 has central alignment guide slots 62 defined therein. The lower circuit board 60 is arced to match the curve defined by slot 50 and selectively received therein. Before being inserted in the spacer members, while the printed circuit board material is still flat, a plurality of locator apertures 64 are defined. Each aperture is precisely cut to receive a brush 70 therethrough.

With continuing reference to FIG. 3 and further reference to FIG. 5, each brush 70 includes a flat thin, generally rectangular tip portion 72 constructed of a silver/teflon material. The tip portion is anchored in a mounting collar 74 which is attached to an elongated shaft or post position 76. Each aperture 64 is defined to receive the tip portion 72 and the socket 74 in a freely sliding relationship therethrough. Yet, the locator apertures 64 are sufficiently close to the outer cross-sectional area of the tip that the tip is restrained against significant wobbling or canting. At an opposite end from the tip, the post defines an electrical connection portion 78.

With reference again to FIGS. 2–4, an upper printed circuit board so defines alignment apertures 82 which receive alignment projections 56. Threaded connectors or other suitable means 84 constrain the upper circuit board 80 to follow arcuate surface 52 of the spacer plates 44. Each upper circuit board 80 has a plurality of shaft receiving apertures 86 drilled therethrough. The apertures 86 are positioned to be in radial alignment with the locator apertures 64 and have a diameter which slidably receives the shaft portion 76 of the brush assemblies. Again, the tolerance between the shaft 76 and the apertures 86 is such that wobbling or other non-radial movement of the brush is restrained. A mounting post or contact 88 is mounted to the circuit board in circumferencial alignment with each brush receiving aperture 86. The printed circuit board so is etched such that electrical connections are provided between each of the electrical contact posts 88 and appropriate sockets of one or more of electrical connectors 90. Test points 92 are provided in each electrical path to provide ready connection to test equipment from each individual brush.

After the side and spacer plates are connected together with the upper and lower circuit boards affixed arcuately, each brush assembly is inserted from the lower side. That is, a coil spring 100 which butts against the mounting collar 74 is received on the shaft 76. The connector end 78 of the post is inserted through apertures 64 and then through aperture 86. The spring 100 abuts a lower surface of the upper circuit board surrounding apertures 86 urging the brush tip 72 to extend. A retainer 102 is slipped over post 76 where it extends above upper circuit board 80 and is releasably anchored thereto to prevent the brush 70 from being propelled out of the circuit boards by the spring 100. Electrical shunt leads 104 having like electrical friction connectors 106 at either end are snap connected to the electrical connection 78 at one end of each brush assembly and to the circumferencially neighboring contact post pin 88. Each shunt lead 104 is selected to be of a soft flexible wire with a minimal spring constant such that it flexes freely with movement of the brush assembly. It will be noted that the lead 104 undergoes rolling motion, rather than flexing motion, greatly increasing its life expectancy. Moreover, each of the leads are positioned parallel to one of the slip ring tracks, i.e. parallel to each other. Thus, none of the leads cross or press against each other reducing the potential for cross talk. It will also be noted that if the friction connectors 106 anchor sufficiently strongly to the connector end 78 of the brush assembly, the retainer 102 may be eliminated. The retainer 102 or other anchoring mechanism for the brush assemblies is only needed until the brush assemblies are installed against the slip ring assembly or when the brush block assembly is, for some reason, removed. While in its installed location, the slip rings prevent the brush assemblies from separating from the brush block.

With particular reference to FIG. 5, each brush 70 is designed to have a low mass. Preferably, it is constructed from a scintered silver/polymer alloy. The silver provides good electrical conduction while the polymer, preferably teflon, acts as a lubricant on the contact interface. The leading edge of the tip is at an angle 108, e.g. a few degrees. The angle is selected to shift the point of contact between the brush and the slip ring to be slightly behind the central axis of the brush, i.e. a trailing point of contact. A point of contact which leads the central axis tends to chatter analogous to pushing chalk across the blackboard; whereas, the trailing point of contact is more analogous to dragging chalk across a blackboard. This angle successfully eliminates audible noise which results from brush vibration and chatter. Due to the low mass of the brush assembly, the spring 100 needs only a very low spring rate to maintain contact with the slip ring.

Figure 7:
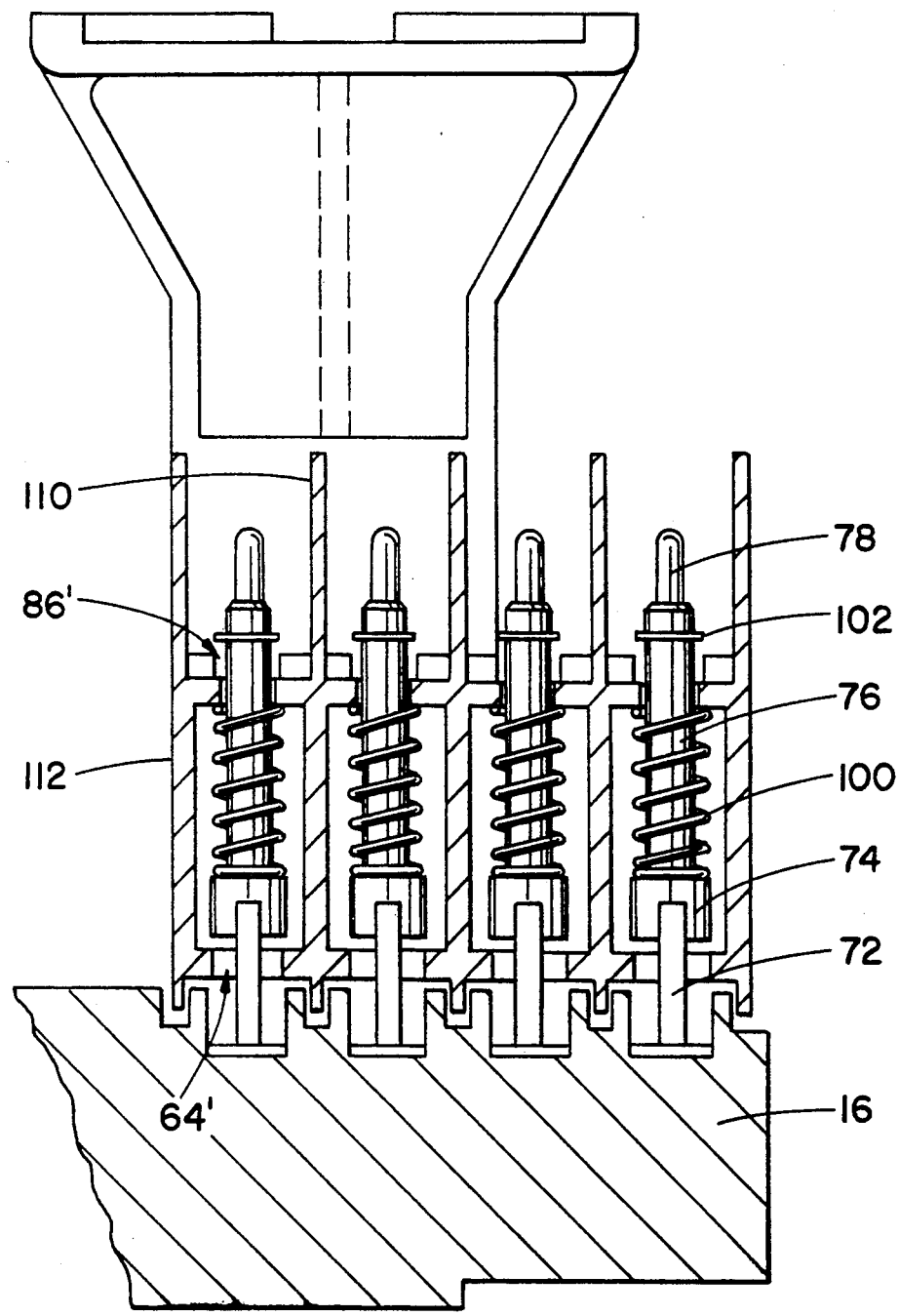
FIG. 7 is a sectional view through section 7—7 of FIG. 6.

With reference to FIGS. 2, 6, and 7, the frame assembly 40 can also be constructed of a plurality of like frame blocks 110. For cosmetic and space purposes, end blocks 112 are only about a half of the central blocks. The end blocks can be made from the same mold by using a plate to close off about half of it.

Each of the blocks 110 have a lower arcuate surface portion 60' which defines half of lower locator apertures 64'. When two blocks are abutted tightly together with their alignment pins 56' received in alignment apertures 82', the locator aperture 64' conform closely with the cross-section of brush tip portion 72 and the anchoring collar 74 portions thereof. Each block assembly further defines second or shaft apertures 86' disposed in radial alignment through the center of the locator apertures 64'. The apertures 86' are defined to receive the shaft portion 76 of a brush assembly in snug but freely sliding relationship. The shaft and locator apertures are radially spaced by about 1½-2 times the tip length or more to improve the stability with which the tip is positioned.

After the mounting blocks 110, 112 are anchored together with bolts or other suitable anchoring means 48', the brush assemblies 70 with springs 100 are inserted through the locator apertures 64'. The shafts 76 are inserted through the shaft apertures 86' as the spring 100 abuts a lower surrounding surface. A retainer 102 retains the brush assembly from being ejected by the spring 100. An electrical shunt lead 104' has a friction connector 106 which frictionally engages electrical connection portions 78 of the brush shaft and a second electrical connector portion 106' which is anchored to a terminal post 88'. The lead portion 104 again rolls on a large radius rather than flexing on a tight radius greatly increasing its resistance to fatigue failure. The leading edge of the tip 72 is again beveled so that it contacts the slip ring at a point which trails its central axis.

To prevent electrical arcing in high voltage slip rings/brush block assemblies, electrical contact portions 120 of the slip ring 16 are mounted in grooves 122 of an insulative material. This blocks line of sight arcing between the contact points between brushes tips 72 and the electrical contact ring 120. To prevent any line of sight arcing between the bushes themselves or other electrically conducted elements, the slip ring further defines a plurality of circumferential grooves 124 between each groove 122. Each of the mounting blocks 110 has a downward projecting shield portion 126 which is received in the circumferencial grooves 124.

The brush block assembly is mounted with the apertures defined between each mounting block in circumferencial alignment with the slip ring. The two brushes received in these two sets of apertures contact the same electrical conductor portion in the slip ring, i.e. provide a redundant electrical path, in high power applications, the redundant path helps prevent arcing. With two brushes, the probability that at least one will be in contact with the slip ring at all times increases tremendously. If the other brush should bounce or lose direct contact with the slip ring, electrical resistance through the brush still in contact will be much lower than the electrical resistance through the air gap of the bouncing brush. Hence, current will tend to flow through the brush in direct contact rather than one which is skipping. Similarly, when signals are sent through the brushes, the dual brushes provide parallel signal paths. If one of the paths is momentarily broken by a brush skipping, electrical continuity is still maintained through the other.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. In a CT scanner that includes a stationary gantry portion having a patient receiving region and a rotating gantry portion on which an x-ray tube is mounted for rotation about the patient receiving region with a slip ring around the patient receiving region connected to one of the stationary and rotary gantry portions, and a brush block assembly mounted on the other gantry portion in siding communication with the slip ring, the brush block assembly comprising:

a plurality of brushes, each brush including a tip portion connected with an elongated shaft portion;

a frame assembly including:

a first circuit board which is flexed along a first arc segment and defines shaft apertures for slidably receiving the shaft portions, a second circuit board which is flexed along a second arc segment generally concentric with the first arc segment and which defines locator apertures therethrough for slidably receiving the tip portions, a pair of identical spacer plates for holding the first and second circuit boards flexed along the first and second arc segments, the spacer plates being symmetric with one rotated 180° relative to the other;

a spring means for resiliently urging a leading edge of the brush tip portion into sliding contact with the slip ring.

2. The brush block assembly as set forth in claim 1 further including a pair of side plates which interconnect the spacer plate together and provide a mounting means for mounting the brush block assembly to the rotating gantry portion, the side plates being identical.

3. In a CT scanner that includes a stationary gantry portion having a patient receiving region and a rotating gantry portion on which an x-ray tube is mounted for rotation about the patient receiving region with a slip ring around the patient receiving region connected to one of the stationary and rotary gantry portions, and a brush block assembly mounted on the other gantry portion in sliding communication with the slip ring, the brush block assembly comprising:

a plurality of brushes, each brush including a tip portion connected with an elongated shaft portion at least the tip portion of each brush being constructed of a silver/polymer alloy such that it has a light mass and low inertia, the silver providing good electrical conductivity, and the polymer providing lubrication;

a frame assembly including a first printed circuit board which is flexed along a first arc segment and defines shaft apertures for slidably receiving the shaft portions of each brush,, such that the shaft portion extends radially relative to the slip ring;

a spring means for resiliently urging a leading edge of the brush tip portion into sliding contact with the slip ring.

4. The brush block assembly as set forth in claim 3 wherein the frame assembly further includes a second circuit board which is flexed along a second arc segment generally parallel tot he first arc segment and which defines locator apertures therethrough for slidably receiving the tip portions.

5. In a CT scanner that includes a stationary gantry portion, a rotatable gantry portion which supports an x-ray tube and is mounted for rotation about a patient receiving region, a slip ring which extends around the patient receiving region and is connected to one of the stationary and rotatable gantry portions, and a brush block assembly which is connected with the other gantry portion in sliding communication with the slip ring, the brush block assembly comprising:

a plurality of brushes, each brush including a tip portion connected to a first end of an elongated shaft, the shaft defining a male electrical connector portion at a second end of the shaft;

a frame assembly including a means for slidably receiving the tip portion and the shaft of each brush such that the shaft portion extends radially relative to the slip ring, the male connector portion extending radially beyond the slidably receiving means providing unrestricted access to the male connector portion;

a flexible electrical lead assembly including a female friction connector which frictionally engages the male connector portion and is supported in axial alignment therewith and an electrical lead which extends from the female friction connector radially relative to the slip ring and in a rolling arc to an electrical contact on the frame assembly;

a spring means for resiliently urging a leading edge of the brush tip portion into sliding contact with the slip ring.

6. In a CT scanner that includes a stationary gantry portion, a rotatable gantry portion which supports an x-ray tube and which is mounted for rotation about a patient receiving region, a slip ring that extends around the patient receiving region and is connected to one of the stationary and rotatable gantry portions, and a brush block assembly which is connected with the other gantry portion in sliding communication with the slip ring, the brush block assembly comprising:

a plurality of brushes, each brush including a tip portion connected with one end of an elongated shaft and a brush connector portion at a second end of the elongated shaft;

a frame assembly including:

a first circuit board which is flexed along a first arc segment and defines shaft apertures for slidably receiving the brush shafts, the first circuit board defining electrically conductive paths to each of a plurality of circuit board connector portions, each circuit board connector portion being disposed adjacent one of the shaft apertures, a second circuit board which is flexed along a second arc segment and which defines locator apertures therethrough for slidably receiving the tip portions, a means for holding the first and second circuit boards flexed along the first and second arc segments and positioned such that the brush shaft portions extend generally radially relative to the slip ring;

a spring means for resiliently urging a leading edge of the brush tip portion into sliding contact with the slip ring;

a plurality of electrical leads, each electrical lead extending in an arc and having a first connector portion connected with one of the brush connector portions and a second connector portion connected with one of the circuit board connector portions.

7. In a CT scanner that includes a stationary gantry portion having a patient receiving region and a rotating gantry portion on which an x-ray tube is mounted for rotation about the patient receiving region with a slip ring around the patient receiving region connected to one of the stationary and rotary gantry portions, and a brush block assembly mounted on the other gantry portion in sliding communication with the slip ring, the brush block assembly comprising:

a plurality of brushes, each brush including a tip portion connected with an elongated shaft portion;

a frame assembly including a plurality of like mounting blocks, pairs of which like mounting blocks meet together to define at least one brush shaft receiving slide path for slidably receiving the brush shaft and tip portions, such that the shaft portion extends radially relative to the slip ring;
a spring means for resiliently urging a leading edge of the brush tip portion into sliding contact with the slip ring.

8. In a CT scanner that includes a stationary gantry portion having a patient receiving region and a rotating gantry portion on which an x-ray tube is mounted for rotation about the patient receiving region with a slip ring which has electrically conductive rings extending around the patient receiving region connected to one of the stationary and rotary gantry portions, and a brush block assembly mounted on the other gantry portion in sliding communication with the slip ring, the brush block assembly comprising:
a plurality of brushes, each brush including a tip portion connected with an elongated shaft portion;
a frame assembly including a plurality of mounting blocks which define brush shaft receiving slide paths for slidably receiving the brush shaft and tip portions, such that the shaft portions extend radially relative to the slip ring, each mounting block including a downward pending flange which extends between the electrically conductive rings of the slip ring to inhibit arcing;
a spring means for resiliently urging a leading edge of the brush tip portion into sliding contact with the slip ring.

9. In a CT scanner that includes a stationary gantry portion having a patient receiving region and a rotating gantry portion on which an x-ray tube is mounted for rotation about the patient receiving region with a slip ring around the patient receiving region connected to one of the stationary and rotary gantry portions, and a brush block assembly mounted on the other gantry portion in sliding communication with the slip ring, the brush block assembly comprising:
a plurality of brushes, each brush including a generally planar tip portion which is enlarged relative to an elongated shaft portion, the tip portion being connected with an elongated shaft portion, at least the tip portion of each brush being constructed of a silver/polymer alloy such that it has a light mass and low inertia, the silver providing good electrical conductivity, and the polymer providing lubrication;
a frame assembly including a means for slidably receiving the tip portions of the brushes and the shaft portions of each brush, such that the shaft portion extends radially relative to the slip ring;
a spring means for resiliently urging a leading edge of the brush tip portion into sliding contact with the slip ring.

10. The brush block assembly as set forth in claim 9 wherein the tip portion has a leading edge in contact with an electrically conductive ring of the slip ring, the leading edge being angled such that a point of primary contact between the leading edge and the electrically conductive ring trails a central axis of the shaft portion during relative rotation of the slip ring and brush block assembly.

11. The brush block assembly set forth in claim 1 further including a flexible electrical lead having a friction connector that is connected to an end of the brush shaft disposed opposite to the tip and which lead extends in a rolling arc to an electrical contact.

12. A brush block assembly comprising:
a plurality of brushes, each brush including a flat tip portion connected with an elongated shaft portion each brush tip portion being constructed of a silver/polymer alloy such that it has a light mass and low inertia, the silver providing good electrical conductivity, and the polymer providing lubrication;
a means for slidably receiving the brushes including a first printed circuit board which is flexed into a first arc segment which is generally concentric with the slip ring, the first printed circuit board defining shaft apertures for slidably receiving the shaft portions of each brush, such that the shaft portion extends radially relative to an associate slip ring;
a spring means for resiliently urging the brush tip portion into sliding contact with the slip rings.

13. The brush block assembly as set forth in claim 12 wherein the means for slidably receiving the brushes include a second circuit board section which is flexed into a second generally concentric with the first circuit board arc segment and which defines locator apertures for slidably receiving the tip portions.

14. A brush block assembly comprising:
a plurality of brushes, each brush including a flat tip portion connected with an elongated shaft portion;
a frame assembly including:
a first printed circuit board which is flexed into a first arc segment which is generally concentric with an associated slip ring, the first printed circuit board defining shaft apertures for slidably receiving the shaft portions,
a second circuit board section which is flexed into a second arc segment generally concentric with the first circuit board arc segment and which defines locator apertures for slidably receiving the tip portions,
a pair of identical spacer plates for holding the first and second circuit boards flexed along the arc segments, the spacer plates being symmetric with one rotated 180° relative to the other, such that the shaft portion extends radially relative to an associate slip ring;
a spring means for resiliently urging the brush tip portion into sliding contact with the slip rings.

15. A brush block assembly comprising:
a plurality of brushes, each brush including a flat tip portion connected with an elongated shaft portion;
a plurality of like mounting blocks pairs of which meet together to define a flat tip portion receiving slide path and a shaft portion slide path therebetween, which path slidingly receives the brush shaft and tip portions such that the shaft portion extends radially relative to an associate slip ring;
a spring means for resiliently urging the brush tip portion into sliding contact with the slip ring.

16. The brush block assembly set forth in claim 15 further including a flexible electrical lead having a friction connector that is connected to an end of the brush shaft disposed opposite to the tip and which lead extends in a rolling arc to an electrical contact.

17. The brush block assembly as set forth in claim 15 wherein each mounting block includes a downward pending flange which extends between electrically conductive rings of the slip ring for inhibiting arcing.

18. A brush block assembly comprising:

a plurality of brushes, each brush including a flat tip portion connected with an elongated shaft portion, the shaft portions being smaller in transverse cross section than the tip portions, each brush tip portion being constructed of a silver/polymer alloy such that it has a light mass and low inertia, the silver providing good electrical conductivity, and the polymer providing lubrication;

a frame assembly including a means for slidably receiving the tip portions of the brushes and the receiving shaft portions of each brush, such that the shaft portion extends radially relative to an associate slip ring;

a spring means for resiliently urging the brush tip portion into sliding contact with the slip rings.

19. The brush block assembly as set forth in claim 18 wherein the tip portion has a leading edge in contact with electrically conductive rings of the slip ring, the leading edge being angled such that a point of primary contact between the leading edge and an associated slip ring trails a central axis of the shaft portion during relative rotation of the slip ring and brush block assembly.

* * * * *